United States Patent [19]

Kubota

[11] 4,344,436
[45] Aug. 17, 1982

[54] DEVICE FOR DETERMINING LOCATION OF THE TIP OF CATHETER

[76] Inventor: Yukio Kubota, No. 1-12, Uenohigashi 1-chome, Toyonaka-shi, Osaka-fu, Japan

[21] Appl. No.: 200,017

[22] Filed: Oct. 23, 1980

[30] Foreign Application Priority Data

Jan. 16, 1980 [JP] Japan .............................. 55-5259[U]
Mar. 31, 1980 [JP] Japan ................................. 55-42705

[51] Int. Cl.³ ............................................. A61M 25/00
[52] U.S. Cl. ................................. 128/350 R; 128/773; 128/207.15; 128/DIG. 9
[58] Field of Search ................... 128/DIG. 9, 772, 773, 128/207.14, 207.15, 716, 720, 4, 350 R, 276

[56] References Cited

U.S. PATENT DOCUMENTS 3,638,655 2/1972 Doherty .......................... 128/207.15

FOREIGN PATENT DOCUMENTS 214014 3/1968 U.S.S.R. .............................. 128/716
401351 2/1974 U.S.S.R. .............................. 128/716

Primary Examiner—Henry J. Recla
Attorney, Agent, or Firm—Armstrong, Nikaido, Marmelstein & Kubovcik

[57] ABSTRACT

A device for determining the location of a catheter in the bronchi comprising a catheter to be inserted into the bronchi, a sound signal generator connected to the proximal end of the catheter, a sound signal receiver for receiving the sound signal which is sent from the sound signal generator into the catheter and released from the distal end of the catheter. According to the device of the invention, there can be easily, exactly and safely determined the position of the tip of the catheter inserted into the bronchi.

5 Claims, 7 Drawing Figures

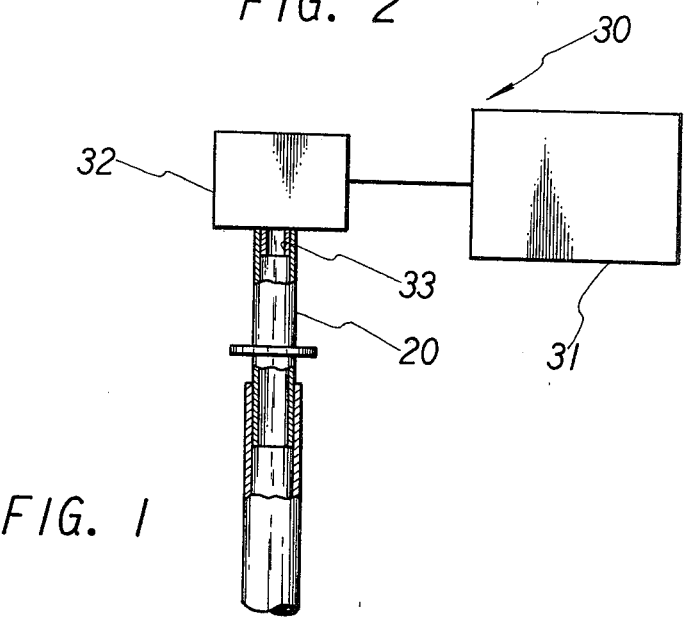
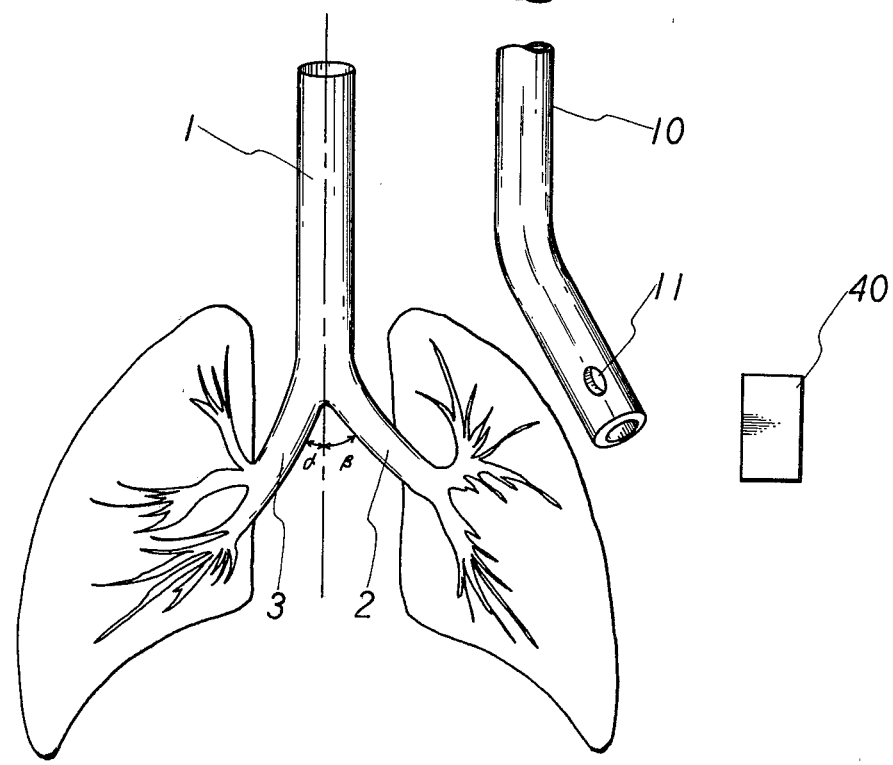
FIG. 2
FIG. 1

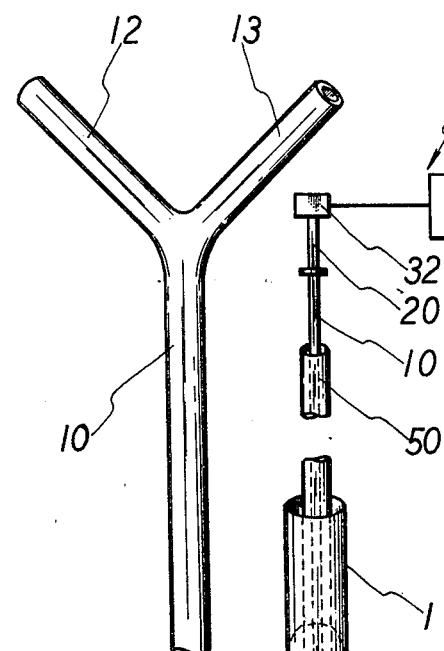
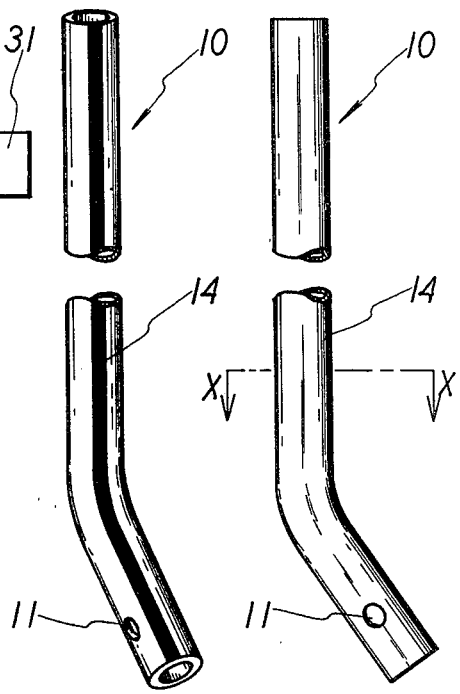
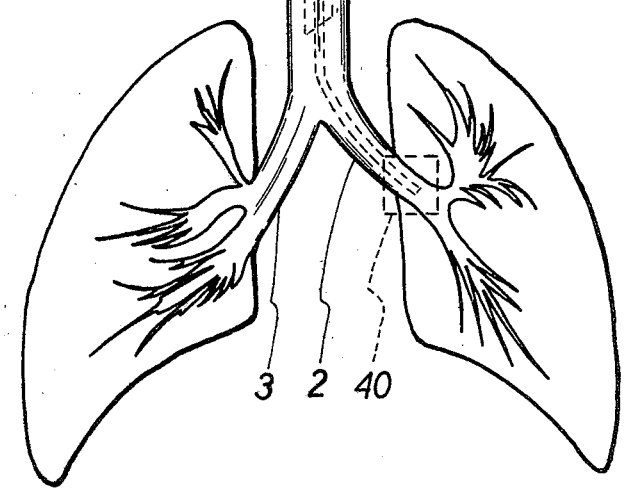
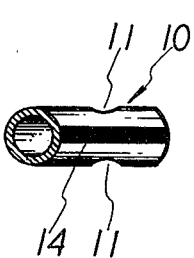
FIG. 4
FIG. 5  FIG. 6
FIG. 3
FIG. 7

DEVICE FOR DETERMINING LOCATION OF THE TIP OF CATHETER

BACKGROUND OF THE INVENTION

The present invention relates to a device for determining the location of a catheter in the bronchi and determining pathological condition in the thorax, and more particularly to a device for determining the position of the distal end, i.e. the tip, of a suction catheter inserted into the bronchi, and for determining pathological condition such as pulmonary edema, pleural effusion, hemothorax, pyothorax, pneumothorax, or neoplasm of the lung.

It is very important for maintaining the life in clinical medicine, particularly in respiratory care of patients under the anesthesia or respiratory insufficiency to remove secretions such as sputum in the bronchi. Removal of secretions is effected by inserting a pliable plastic or rubber suction catheter through either an endotracheal tube or a tracheostomy cannula introduced into the trachea, guiding it into the right or left main bronchus so that the tip is located at the desired position, and sucking the secretions.

In the adult lung, as shown in FIG. 1, the right and left bronchi 2 and 3 which branch off from the lower end of the trachea 1 have different inclinations. The angle $\alpha$ of the right bronchus 3 to the tracheal axis is about 25° in the average and is smaller than the angle $\beta$ of the left bronchus 2 which branches off from the trachea 1 at an angle of about 45° in the average. Thus, the tip of the suction catheter inserted through an endotracheal tube or a tracheostomy cannula is easy to enter the right bronchus 3 and is hard to enter the left bronchus 2. Accordingly, the suction of the left bronchus is more difficult than the right bronchus, and the incidence of pulmonary complication on the left lung is higher than on the right lung.

Various techniques and procedures have been attempted and applied to the selective suction of the left bronchus, such as the use of a straight or curved-tip suction catheter, turning the head of patient to the right side and turning the body of patient to the left or right side. However, a definite technique which allows the catheter to selectively introduce into and suck the left bronchus has not yet been established.

A curved-tip catheter is designed so as to be selectively inserted into the desired bronchus with good success. The catheter is inserted through an endotracheal tube or a tracheostomy cannula with the curved-tip directed to the bronchus to be inserted. It is necessary to direct the curved-tip to the bronchus to be inserted during the insertion, but the catheter rotates or twists during the insertion and, therefore, it is difficult to surely insert the tip of the catheter into the desired bronchus.

Also, there is no simple method to determine the location of the tip of catheter, even if the tip enters into the left bronchus. In order to perform the selective bronchial suction, it is necessary to surely determine the position of the tip of the catheter. X-ray monitoring and scintiphotographic technique have been employed for ensuring the positioning of catheter. However, these techniques are not readily available in most situations. In addition, these techniques involve radiation exposure. Bronchoscopy has also been employed when a retained secretion or a foreign body may cause persistent obstruction atelectasis. However, bronchoscopy must be effected by a physician skilled in the technique.

Accordingly, there is desired the development of a device or technique for determining the position of the tip of catheter, which is simple and safe and is usable for anybody at anytime and anywhere. Such a device or technique is of great use for the prevention and treatment of pulmonary complications, for instance, after operations, and greatly contributes to clinical medicine.

On the other hand, auscultation, fluoroscopy, roentgenography, scintiphotography and echography have been used to diagnose pathological condition in the thorax such as pulmonary edema, pleural effusion, hemothorax, pyothorax, pneumothorax or neoplasm of the lung. These techniques are not always safe, simple or easy and readily available except auscultation. Accordingly, there is also desired a development of a method or device which can detect a pathological condition more exactly than auscultation and more safely, simply and easily than fluoroscopy, roentgenography, scintiphotography and echography.

SUMMARY OF THE INVENTION

It is an object of the present invention to provide a device for determining easily, surely and safely the position of the tip of a suction catheter inserted into the bronchi.

A further object of the present invention is to provide a device for determining easily, surely and safely a pathological condition in the thorax.

Another object of the present invention is to provide a catheter capable of selectively inserting into the left or right bronchus.

These and other objects of the present invention will become apparent from the description taken with the accompanying drawings.

In accordance with the present invention, there is provided a device for determining the location of the tip of a catheter in the bronchi and a pathological condition in the thorax comprising a catheter to be inserted into the bronchi, a sound signal generator connected to the proximal end of said catheter, a sound signal receiver for receiving the sound signal which is sent from the sound signal generator into the catheter and released from the distal end of the catheter.

BRIEF DESCRIPTION OF THE DRAWINGS

FIG. 1 is an illustrative view showing the bronchi;

FIG. 2 is a schematic view showing an embodiment of a device of the present invention;

FIG. 3 is an illustrative view showing the state of using a device of the present invention;

FIG. 4 is a partial perspective view showing an embodiment of a catheter used in a device of the present invention;

FIG. 5 is a perspective view showing another embodiment of a catheter used in a device of the present invention;

FIG. 6 is a side view of the catheter shown in FIG. 5; and

FIG. 7 is a section view taken on line X—X of FIG. 6.

DETAILED DESCRIPTION

The device of the present invention is explained below with reference to the drawings.

In FIG. 2, reference numeral 10 is a catheter, and a sound signal generator 30 is connected to the proximal end of the catheter 10 through a connecting tube 20. The sound signal generator 30 consists of a main body 31 provided with a power circuit portion, an oscillator and an amplifier, and a signal converter 32 for converting an electric signal to a sound signal which is connected to the main body 31. A sound signal outlet 33 of the convertor 32 is connected to the connecting tube 20. The sound signal sent from the sound signal generator 30 into the catheter 10 and released from the distal end, i.e. the tip, of the catheter is received by a sound signal receiver 40.

As shown in FIG. 3, through an endotracheal tube or tracheostomy cannula 50 inserted into the trachea 1, the catheter 10 is introduced and its tip enters into either the left bronchus 2 or the right bronchus 3. The sound signal generator 30 is then connected through the connecting tube 20 to the catheter 10, and a sound signal is sent into the catheter 10. The sound signal is transmitted through the catheter 10 to its tip and is sent forth therefrom. Under such a condition, there is looked for a place where the sound signal is the strongest by the sound signal receiver 40 held to the chest wall to determine the position of the tip of the catheter 10. Thus, it is possible to exactly, easily and safely determine whether the catheter 10 enters the left bronchus 2 or the right bronchus 3 and at what part of the bronchus the tip of the catheter 10 locates. After positioning the tip at the desired part of the left or right bronchus, the sound signal generator 30 is removed from the proximal end of the catheter 10, and a suitable vacuum source is connected to the proximal end of the catheter to conduct suction of secretions.

The sound signal sent forth from the tip of the catheter 10 is attenuated until it reaches the sound signal receivers 40 through the chest wall. The degree of the attenuation varies largely depending on pathological conditions such as pulmonary edema, pleural effusion, hemothorax, pyothorax, pneumothorax and neoplasm of the lung. Therefore, according to the device of the present invention, it is also possible to know or determine the pathological condition in the thorax on the basis of the strength of the sound signal detected by the receiver 40.

In the present invention, the sound signal may be audible sounds or supersonic waves. Suitable signal generator 30 and signal receiver 40 are adopted according to the kind of the signal such as audible sound or supersonic wave, or the frequency thereof. For instance, in case of using an audible sound as a sound signal, an earphone may be used as a converter 32 and a stethoscope or electric stethoscope may be used as a signal receiver 40. In case of detecting the pathological condition in the thorax, as a sound signal receiver 40 there is desired a receiver of a type such that the signal strength can be shown on a cathode-ray tube or can be automatically recorded.

Although the frequency of the sound signal is not limited particularly, a frequency band of as small attenuation as possible is preferred. In case of using an audible sound, a frequency of 200 to 800 Hz is the most suitable from this point of view. The sound signal may be a continuous signal or an intermittent signal. An intermittent signal has a tendency to be easy to hear.

The catheter 10 employed in the present invention is not particularly limited, and a pliable tube made of rubbers or plastics is usually employed as a catheter. The distal end portion of the catheter 10 may be straight one or a curved one as shown in FIG. 2. A curved-tip catheter has the advantage of being easy to insert selectively into the right or left bronchus. In case that the catheter 10 is employed for the suction of secretions, one or more suction holes 11 may be provided on the wall of the distal end portion of the catheter 10 in order to make the suction easy.

Also, as shown in FIG. 4, the proximal end of the catheter 10 may be forked, one being a joint or leg 12 for connecting with the sound signal generator 30 and the other being a joint or leg 13 for connecting with an oxygen supply source. When an oxygen supply source is connected to the joint 13 and oxygen is supplied, it is possible to detect the location of the tip of the catheter 10 and the pathological condition in the thorax while ventilating lung with 100% oxygen. A three-forked connecting tube may be used as a connecting tube 20 instead of the forked catheter. Also, oxygen may be supplied through the gap between the endotracheal tube or tracheostomy cannula 50 and the catheter 10.

In the device as shown in FIG. 2, suction of secretions is conducted after removing the signal generator 30 from the catheter 10 and connecting a vacuum source to the catheter 10. When a three-way stop cock is used as a connecting tube 20 and connected to the catheter 10, the signal generator 30 and a vacuum source respectively, reception of sound signal and suction of secretions can be alternately conducted by only switching the cock.

A catheter which is pliable and has a curved distal end portion and a mark for guiding the insertion on its circumference is the most preferably employed in the present invention. FIG. 5 is a perspective view showing an embodiment of such a catheter. FIG. 6 is a side view of the catheter shown in FIG. 5, and FIG. 7 is a section view taken on line X—X of FIG. 6. In FIGS. 5 to 7, the distal end portion of the catheter 10 is curved, and also the catheter 10 has a guide mark 14 extending lengthwise and straight over almost full length on the surface of the curved side, the mark 14 being straight when looked from the curved side. In case of employing such a catheter 10, the direction of the curved-tip can be maintained without rotation of the catheter during the insertion by sending the catheter into the endotracheal tube or tracheostomy cannula 50 with the mark directed to a constant direction. Accordingly, when the catheter 10 is inserted into the endotracheal tube or tracheostomy cannula 50, for instance, with the curved-tip directed to the left lung and is then sent into the tube or cannula 50 with the mark directed to a constant direction, the tip of the catheter can be easily introduced into the left bronchus. Also, even if the catheter 10 rotates in the endotracheal tube or trachea, the direction of the curved-tip can be revised so as to direct to a correct direction by returning the mark 14 to the original direction. Since the catheter 10 is pliable, it may twist during the insertion. In that case, the twist is eliminated and the direction of the curved-tip is revised correctly by a procedure such as rotating the catheter right and left or swaying the catheter slightly.

The guide mark 14 is in general a line such as a solid line, a broken line or a dotted line. Although the guide mark 14 is usually provided on the surface of the side to which the tip is curved, it may be provided on the opposite side or on the both sides. The guide mark 14 may be formed in various manners such as printing, coating of a paint, or pigmentation of raw material with a different color at the time of preparing the catheter. A radio opaque material may also be used in forming the guide mark. Also, it is convenient to provide a length scale on the guide mark 14 from the tip, since the position of the tip can be conjectured from the length inserted.

As stated above, according to the device of the present invention, it is possible to easily, safely and exactly determine the location of the tip of the catheter inserted into the bronchi and to selectively conduct prompt and sufficient bronchial suction, and accordingly excellent results can be obtained in the prevention and treatment of pulmonary complications. It is also possible to easily and safely detect a pathological condition in the thorax, and the device of the invention makes a great contribution to early detection and treatment of various diseases in the thorax.

What is claimed is:

1. An apparatus for determining the location of the tip of a catheter in the bronchi, said apparatus comprising catheter tube means for insertion into the bronchi and for removing matter from the bronchi, said catheter tube means including a curved tip at one end thereof and guide mark means extending along the length of said catheter tube means on one side thereof for providing an indication of the direction of said curved tip; a sound signal generator means coupled to the other end of said catheter tube means for generating a sound signal in said catheter tube means such that the sound signal travels through said catheter tube means and exits from said one end thereof; and sound signal receiver means, external to the body, for receiving the sound signal exiting from said one end of said catheter tube means and thereby determining the position of said one end of said catheter tube means within the bronchi.

2. The device of claim 1, wherein the sound signal is an audible sound.

3. The device of claim 2, wherein the frequency of the audible sound is from 200 to 800 Hz.

4. The device of claim 1, wherein the sound signal is a supersonic wave.

5. A device as set forth in claim 1 wherein said other end of said catheter tube means includes a Y-shaped portion and wherein one leg of said Y-shaped portion is coupled to said sound signal generator.

* * * * *